US00RE48103E

(19) United States
(12) Reissued Patent
Shinoda et al.

(10) Patent Number: US RE48,103 E
(45) Date of Reissued Patent: Jul. 21, 2020

(54) TRANSFER SYSTEM

(71) Applicant: PANASONIC INTELLECTUAL PROPERTY MANAGEMENT CO., LTD., Osaka (JP)

(72) Inventors: Masayo Shinoda, Tokyo (JP); Tomoki Masuda, Osaka (JP); Haruka Kusukame, Nara (JP); Mitsuru Harada, Osaka (JP)

(73) Assignee: PANASONIC INTELLECTUAL PROPERTY MANAGEMENT CO., LTD., Osaka (JP)

(21) Appl. No.: 15/952,573

(22) Filed: Apr. 13, 2018

Related U.S. Patent Documents

Reissue of:
(64) Patent No.: 9,526,315
Issued: Dec. 27, 2016
Appl. No.: 14/535,657
Filed: Nov. 7, 2014

U.S. Applications:
(63) Continuation of application No. PCT/JP2014/000848, filed on Feb. 19, 2014.

(30) Foreign Application Priority Data

Mar. 1, 2013 (JP) ..... 2013-040472

(51) Int. Cl.
*A45D 40/26* (2006.01)
*A61M 35/00* (2006.01)
(Continued)

(52) U.S. Cl.
CPC ..... *A45D 40/261* (2013.01); *A45D 33/38* (2013.01); *A45D 40/30* (2013.01); *A45D 44/005* (2013.01);
(Continued)

(58) Field of Classification Search
CPC ..... A61M 37/00; A61M 35/00; A45D 2200/1036; A45D 40/261; A45D 33/38;
(Continued)

(56) References Cited

U.S. PATENT DOCUMENTS 5,556,469 A 9/1996 Koyama et al.
5,904,804 A * 5/1999 Kouda et al. ..... 156/540
(Continued)

FOREIGN PATENT DOCUMENTS

JP 05-013799 1/1993
JP 11-139091 5/1999
(Continued)

OTHER PUBLICATIONS

International Search Report of PCT application No. PCT/JP2014/000848 dated May 20, 2014.

*Primary Examiner* — Sara S Clarke
(74) *Attorney, Agent, or Firm* — McDermott Will & Emery LLP

(57) ABSTRACT

[A transfer system comprises a plurality of rollers configured to provide a rotating function; an endless belt installed on the plurality of rollers; a thin-film having a first surface and a second surface opposite to the first surface; and a functional material adhered on the first surface, the functional material including at least one of a cosmetic material and a medical material. The thin film and the functional material are retained on the endless belt so that the functional material is in contact with the endless belt. The thin film and the functional material are transferred to an adherend so that the second surface is in contact with the adherend.] *A transfer system includes: a thin-film having a first surface and a second surface opposite to the first surface; a functional material adhered on the first surface; and a transfer apparatus having a third surface on which the thin film and the*
(Continued)

*functional material are retained so that the functional material is in contact with the third surface.*

13 Claims, 4 Drawing Sheets

(51) Int. Cl.

| | |
|---|---|
| ***A61K 8/02*** | (2006.01) |
| ***A61Q 17/04*** | (2006.01) |
| ***A61Q 19/08*** | (2006.01) |
| ***A45D 33/38*** | (2006.01) |
| ***A61Q 19/00*** | (2006.01) |
| ***A61Q 19/02*** | (2006.01) |
| ***A45D 40/30*** | (2006.01) |
| ***B41J 2/005*** | (2006.01) |
| ***A45D 44/00*** | (2006.01) |

(52) U.S. Cl.
CPC ..... *A61K 8/0204* (2013.01); *A61Q 17/04* (2013.01); *A61Q 19/007* (2013.01); *A61Q 19/02* (2013.01); *A61Q 19/08* (2013.01); *B41J 2/0057* (2013.01)

(58) Field of Classification Search
CPC ..... A45D 44/005; A45D 40/30; A61Q 1/025; A61Q 19/02; A61Q 19/08; A61Q 19/007; A61Q 17/04; A61K 2800/874; A61K 8/0204; B41J 2/0057
See application file for complete search history.

(56) References Cited

U.S. PATENT DOCUMENTS

| | | | | |
|---|---|---|---|---|
| 2007/0231034 | A1* | 10/2007 | Yasui | G03G 15/231 399/401 |
| 2008/0028967 | A1* | 2/2008 | Sakashita et al. | 101/479 |
| 2010/0119585 | A1* | 5/2010 | Hille | A61K 9/7053 424/449 |
| 2010/0256309 | A1* | 10/2010 | Endo | B29C 55/14 525/384 |
| 2011/0200652 | A1* | 8/2011 | Smith | A45D 26/0014 424/401 |
| 2012/0315067 | A1* | 12/2012 | Takahashi | G03G 15/162 399/302 |
| 2015/0282595 | A1* | 10/2015 | Kimura | A61Q 17/04 132/200 |

FOREIGN PATENT DOCUMENTS

| | | | |
|---|---|---|---|
| JP | 11-169231 | 6/1999 | |
| JP | 11-227390 | 8/1999 | |
| JP | 2001-346627 | 12/2001 | |
| JP | 2003-044837 | 2/2003 | |
| JP | 2004-202768 | 7/2004 | |
| JP | 2006-255088 | 9/2006 | |
| JP | 2011-172831 | 9/2011 | |
| JP | 2012-516284 | 7/2012 | |
| WO | 2010/086901 | 8/2010 | |
| WO | WO 2012/081065 A1 * | 6/2012 | B32B 27/00 |

* cited by examiner

TRANSFER SYSTEM

Matter enclosed in heavy brackets [ ] appears in the original patent but forms no part of this reissue specification; matter printed in italics indicates the additions made by reissue; a claim printed with strikethrough indicates that the claim was canceled, disclaimed, or held invalid by a prior post-patent action or proceeding.

*CROSS REFERENCE TO RELATED APPLICATIONS*

*This application is a reissue application of U.S. Pat. No. 9,526,315 issued on Dec. 27, 2016 issued from U.S. patent application Ser. No. 14/535,657, filed on Nov. 7, 2014, which is a continuation application of PCT International Application No. PCT/JP2014/000848 filed on Feb. 19, 2014, designating the United States of America, which is based on and claims priority of Japanese Patent Application No. 2013-040472 filed on Mar. 1, 2013.*

TECHNICAL FIELD

The present disclosure relates to a transfer device for transferring, to an adherend such as a human body, a thin-film to which a functional material such as a cosmetic agent used, for example, in cosmetic and medical fields adheres[, and to a printing device for generating a thin-film printed body produced by printing a functional material on a thin-film].

BACKGROUND ART

In recent years, methods for facial makeup (hereinafter simply referred to as "makeup") have diversified. This makes it difficult, particularly for people who do not have sufficient knowledge about makeup, to select appropriate makeup from countless options. This is because it takes an enormous amount of time and effort to actually try every makeup to determine and compare the makeup.

In view of the above, for example, PTL 1 and PTL 2 disclose techniques for generating and presenting a simulation image of a face when makeup is applied. Each of the techniques (hereinafter referred to as the "conventional technique") disclosed in these patent literatures acquires an image by photographing a face to which makeup is to be applied. The conventional technique generates a simulation image by superimposing, onto the acquired image, an image that shows a makeup condition when lipstick, blush (rouge), and the like are applied to the face. Each of these conventional techniques then displays the generated simulation image on a display device.

Based on the display image, a user can determine suitability of the makeup without actually applying the makeup for comparison and consideration, thereby allowing selection of appropriate makeup with less time and effort.

However, even when makeup suitable for oneself is proposed with such a simulation image, actually applying the makeup to oneself needs a specific cosmetic agent and a makeup set, and makeup techniques and makeup time of some extent or more.

Accordingly, some users may face difficulty in applying the proposed makeup to themselves or may have to take trouble to request a professional beautician or the like to apply the makeup.

Therefore, for example, if the user is provided with a thin-film to which a functional material such as a cosmetic agent adheres, the thin-film simulating makeup of a professional, and if the user can affix the thin-film on a necessary place by oneself, it is possible to finish professional's makeup even if the user does not apply makeup from the beginning by oneself.

However, since such a thin-film has an ultrathin thickness and requires careful handling, the user cannot affix the thin-film on skin easily by oneself.

Therefore, the present disclosure provides a transfer device for simply transferring, to an adherend such as a human body, a thin-film to which a functional material such as a cosmetic agent used, for example, in cosmetic and medical fields adheres, without damage to the thin-film itself.

CITATION LIST

Patent Literatures

PTL 1: Unexamined Japanese Patent Publication No. 2001-346627

PTL 2: Unexamined Japanese Patent Publication No. 2003-44837

SUMMARY

[A transfer system comprises a plurality of rollers configured to provide a rotating function; an endless belt installed on the plurality of rollers; a thin-film having a first surface and a second surface opposite to the first surface; and a functional material adhered on the first surface, the functional material including at least one of a cosmetic material and a medical material. The thin film and the functional material are retained on the endless belt so that the functional material is in contact with the endless belt. The thin film and the functional material are transferred to an adherend so that the second surface is in contact with the adherend.]

[This configuration allows an ultrathin thin-film to be simply transferred to the adherend such as a human body without damage to the thin-film, the thin-film having the adhered functional material and requiring careful handling.]

*A transfer system includes: a thin-film having a first surface and a second surface opposite to the first surface; a functional material adhered on the first surface; and a transfer apparatus having a third surface on which the thin film and the functional material are retained so that the functional material is in contact with the third surface.*

DESCRIPTION OF EMBODIMENT

Findings Underlying the Present Disclosure

The present disclosure provides a transfer device for simply transferring, to an adherend such as a human body, a thin-film to which a functional material such as a cosmetic agent used, for example, in cosmetic and medical fields adheres, without damage to the thin-film itself.

This enables, for example, people who do not have sufficient knowledge or techniques about makeup and people who cannot take time for makeup to apply makeup easily, quickly, and safely without assistance.

However, since the thin-film has a thickness of the order of nanometers (a material and thickness of the thin-film will be described later), which is so thin that the user does not feel the thin-film is affixed on the skin, handling requires greatest care.

Accordingly, at a time of transfer, the thin-film can be preferably transferred directly from a printing device to a human body without human intervention. This is because affixation of the thin-film on a predetermined place of a human body after the thin-film is once picked up by hand may cause degradation of the thin-film printed body itself or failure in the affixation.

That is, in the present disclosure, in view of the aforementioned problems, a transfer device has been created for easily and securely transferring, to the human body, a delicate thin-film printed body having a directional transfer surface, the thin-film printed body being output from the printing device for the thin-film printed body.

An exemplary embodiment of the present disclosure will be described in detail below with reference to the drawings.

First Exemplary Embodiment

Figure 1:
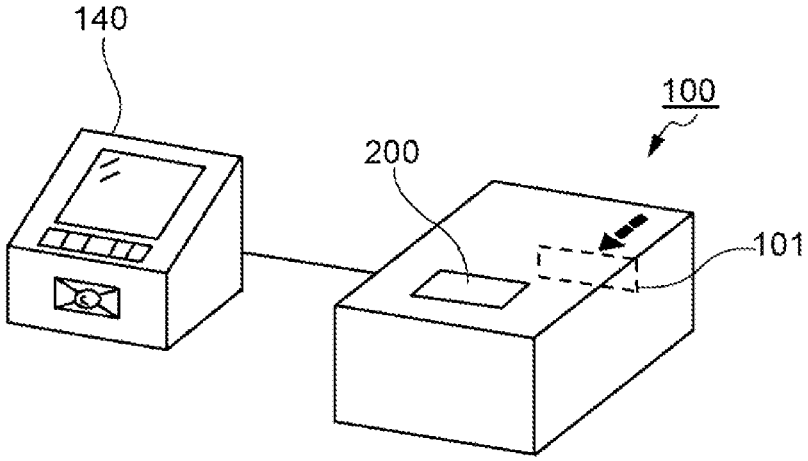
FIG. 1 is a diagram illustrating an external appearance of a printing device according to a first exemplary embodiment of the present disclosure.

FIG. 1 is a diagram illustrating an external appearance of printing device 100 according to a first exemplary embodiment of the present disclosure. Printing device 100 is connected to makeup information terminal 140, and can receive makeup information. Here, makeup information terminal 140 may include an input unit capable of receiving makeup information related to a user, a camera capable of photographing the user oneself, and the like. In addition, makeup information terminal 140 may be connected to a network to obtain makeup information from outside.

Figure 2:
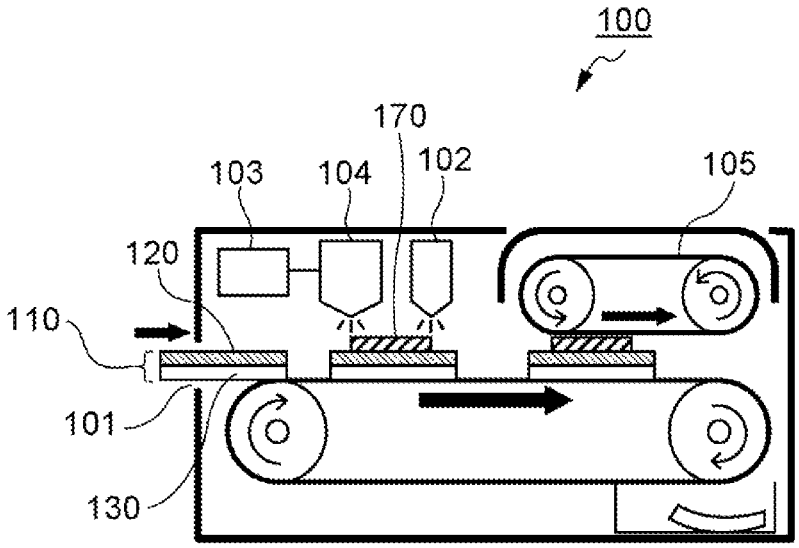
FIG. 2 is a diagram illustrating an internal structure of the printing device according to the first exemplary embodiment of the present disclosure.

FIG. 2 is a diagram illustrating an internal structure of printing device 100 according to the first exemplary embodiment of the present disclosure. FIG. 2 schematically illustrates thin-film sheet 110 fed from thin-film sheet feeder 101 being delivered to transfer unit 105 as thin-film printed body 160.

Figure 4:
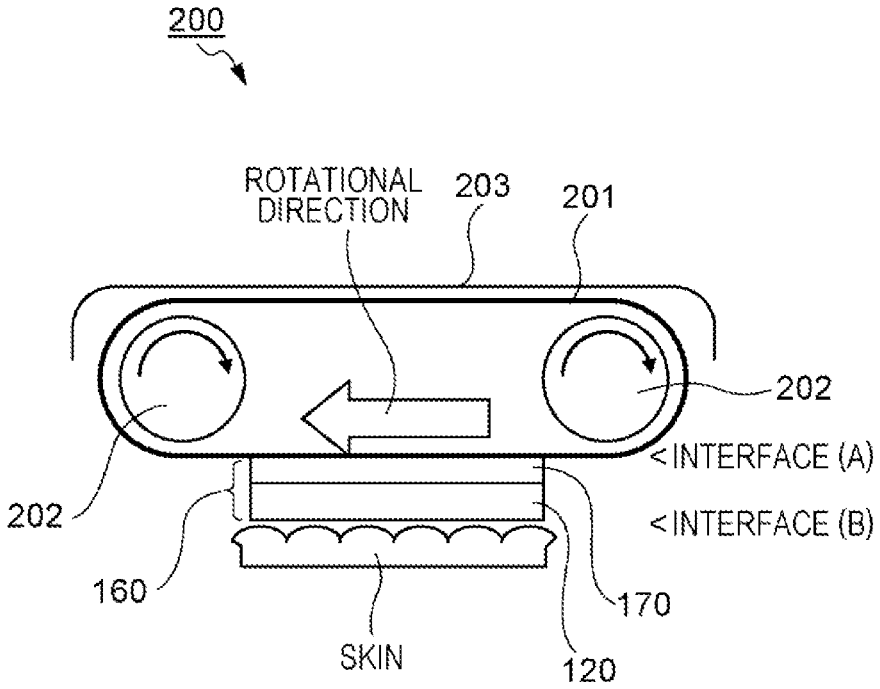
FIG. 4 is a diagram illustrating a configuration of a transfer device according to the first exemplary embodiment of the present disclosure.
Figure 5A:
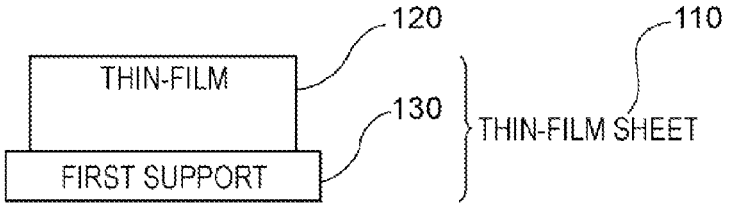
FIG. 5A is a diagram illustrating operations of the printing device and the transfer device according to the first exemplary embodiment of the present disclosure.
Figure 5B:
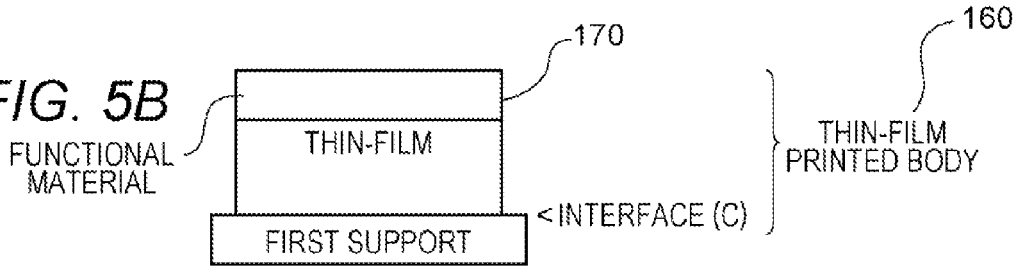
FIG. 5B is a diagram illustrating operations of the printing device and the transfer device according to the first exemplary embodiment of the present disclosure.
Figure 5C:
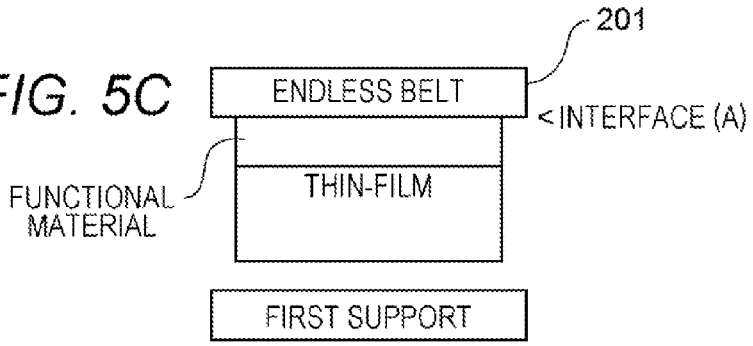
FIG. 5C is a diagram illustrating operations of the printing device and the transfer device according to the first exemplary embodiment of the present disclosure.
Figure 5D:
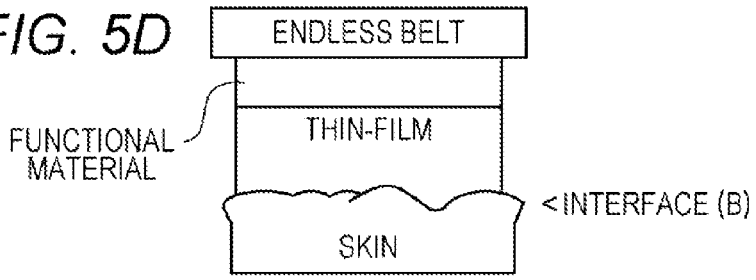
FIG. 5D is a diagram illustrating operations of the printing device and the transfer device according to the first exemplary embodiment of the present disclosure.
Figure 5E:
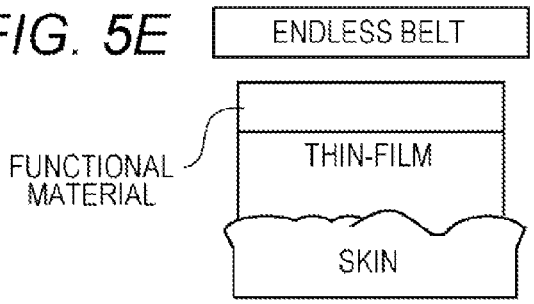
FIG. 5E is a diagram illustrating operations of the printing device and the transfer device according to the first exemplary embodiment of the present disclosure.

With reference to FIG. 4, a description will now be given of a configuration of transfer device 200 according to the first exemplary embodiment of the present disclosure. FIG. 4 is a diagram illustrating the configuration of transfer device 200 according to the first exemplary embodiment of the present disclosure.

Transfer device 200 includes endless belt 201, rollers 202, and grip portion 203. Grip portion 203 is configured as a portion to grip by hand, or means gripping an end of roller 202.

Thin-film printed body 160 with functional material 170 printed on thin-film 120 is retained on endless belt 201. Endless belt 201 causes thin-film printed body 160 to transfer to skin by bringing this thin-film 120 portion into intimate contact with a human body.

A surface of endless belt 201 may, for example, receive surface treatment for increasing hydrophilic properties, have an uneven pattern, or use a temperature-responsive polymer. A concentration of either positive or negative may be increased by applying an electric field or the like.

Appropriate tension is typically applied to endless belt 201 by two rollers 202, thereby improving an adhesive property when being pressed against the skin. When the user holds grip portion 203, presses transfer device 200 against a desired place of the human body, and moves transfer device 200 in a right direction according to printing content, the user can transfer thin-film printed body 160 on which functional material 170 or the like is printed from endless belt 201 onto the skin.

Transfer device 200 is typically incorporated in printing device 100 for producing the thin-film printed body. Transfer device 200 is configured so that thin-film printed body 160 with functional material 170 or the like printed on thin-film 120 can be transferred from printing device 100 on endless belt 201 of transfer device 200.

Figure 3:
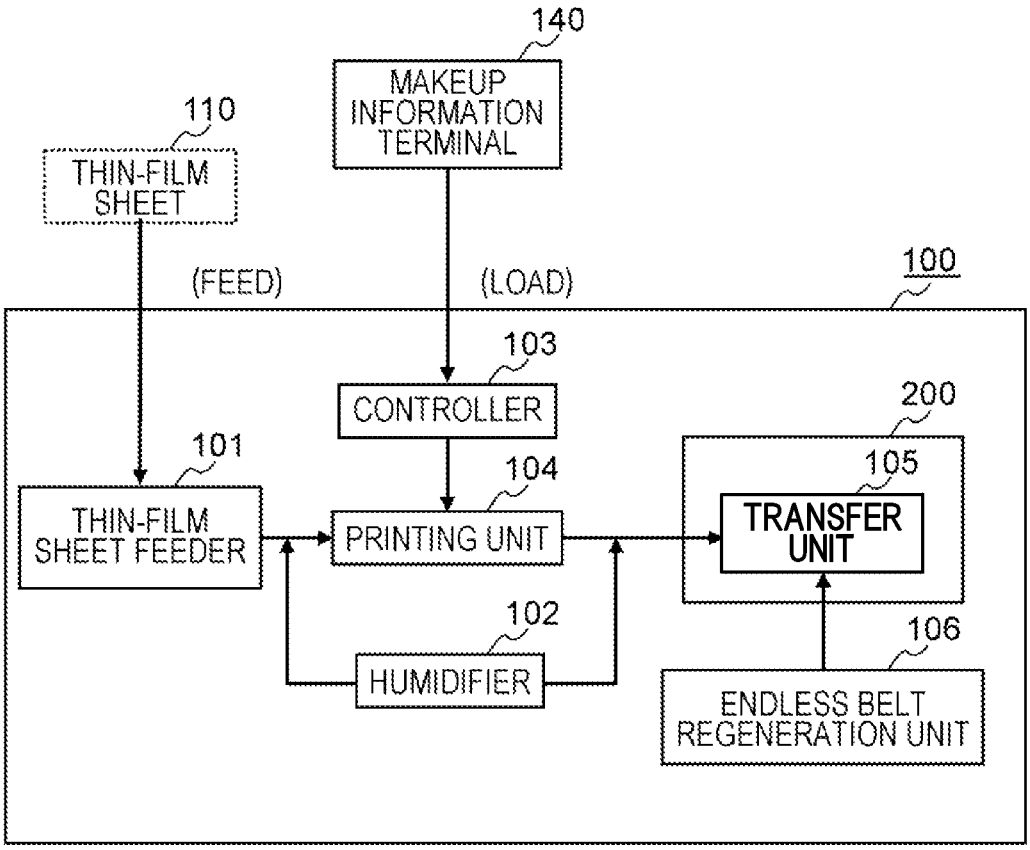
FIG. 3 is a diagram illustrating a configuration of the printing device for a thin-film printed body.

Next, printing device 100 will be described with reference to FIG. 3. FIG. 3 is a diagram illustrating a configuration of printing device 100 for thin-film printed body 160.

Printing device 100 includes thin-film sheet feeder 101, humidifier 102, controller 103, printing unit 104, and transfer unit 105.

Thin-film sheet feeder 101 includes a roller and drive mechanism for feeding thin-film sheet 110 from outside of printing device 100 into inside of printing device 100.

Here, thin-film sheet 110 is thin-film 120 mounted on first support 130 in advance, thin-film 120 serving as a base for printing a functional material 170 or the like. Thin-film sheet 110 is provided, for example, in a form of a seal or a roll.

In such thin-film sheet 110, an interface (C) between thin-film 120 and first support 130 is retained by, for example, static electricity, chemical adsorption, and physical adsorption. A surface of first support 130 of thin-film sheet 110 has, for example, a hydrophilic group.

Thin-film sheet feeder 101 rolls and feeds thin-film sheet 110 into inside of printing device 100 while rotating a roller to avoid damaging thin-film 120 of thin-film sheet 110.

Then, thin-film 120 in thin-film sheet 110 is required to have a characteristic suitable for print of functional materials 170 such as a cosmetic agent and a medical material, and for subsequent affixation on the human body. In other words, the thin-film itself is preferably a biocompatible, safe material that does not have adverse health effects on the human body, such as a stimulus and a hazardous property.

Preferably, a surface of thin-film 120 on a side on which functional material 170 or the like is printed fixes functional material 170 or the like well, and does not allow a component of functional material 170 or the like to penetrate to a surface on an opposite side that is to be affixed onto the human body. This minimizes damage caused by the functional material or the like to the human body.

In addition, a surface of thin-film 120 to be affixed on the human body has an adhesive property capable of coming into intimate contact with skin by itself without the need for another material, such as an adhesive agent. This makes it possible to prevent damage caused by the adhesive agent or the like to the human body, to eliminate a process of adding an adhesive layer to thin-film 120, and to facilitate manufacturing of thin-film printed body 160.

Since thin-film 120 supports functional material 170, such as a printed cosmetic agent, thin-film printed body 160 including thin-film 120 and functional material 170 is adapted to be transferred to skin by being pressed against the skin.

As such a thin-film, for example, a nano thin-film or the like based on a nano sheet of a biocompatible polymer can be used.

Humidifier 102 has a mechanism for humidifying thin-film sheet 110. Humidifier 102 can improve pliability of thin-film 120 and lower an adhesive force of the interface (C) between first support 130 and thin-film 120 by, for example, spraying vapor or water-soluble liquid, or by putting thin-film sheet 110 in water or water-soluble liquid.

Further, humidifier 102 is, for example, humidifier 102 maintained at constant humidity, and humidifies thin-film 120 by putting thin-film 120 in a constant humidity environment. Alternatively, humidifier 102 humidifies thin-film 120 by causing a base material containing water or water-soluble liquid to come into contact with thin-film 120.

Humidifier 102 may be provided before or after printing, or both before and after printing in printing unit 104. However, it is possible to obtain an effect of the present exemplary embodiment even if humidifier 102 is not provided.

Controller 103 generates printing information about how functional material 170 or the like is to be printed on thin-film 120. Controller 103 includes a communication unit for communication with, for example, external makeup information terminal 140, a signal processor, a storage unit, and the like. The generated printing information is sent to printing unit 104 as a printing signal (control signal for a printing operation of a head).

Makeup information terminal 140 with which controller 103 communicates provides makeup information that serves as a base for generating the printing information. The makeup information is, for example, information that shows details of makeup proposed for a user who wants to receive makeup assistance. The makeup information is provided, for example, as an application in makeup information terminal 140 or as cloud service from a server to which makeup information terminal 140 is connected.

Printing unit 104 has a head mechanism for printing functional material 170 on thin-film 120 of thin-film sheet 110 based on the printing signal from controller 103. Printing unit 104 employs a known printing method, for example, a bubble jet method and a thermal dye-sublimation method. The printing method is not limited as long as functional material 170 or the like can be printed well on thin-film 120.

Transfer unit 105 is configured as a transferring unit and functions only when transfer device 200 is incorporated in printing device 100.

Transfer unit 105 transfers thin-film printed body 160 on which functional material 170 is printed by printing unit 104 from first support 130 to endless belt 201 of transfer device 200 without damages to thin-film printed body 160. Transfer unit 105 includes, for example, a roller and a drive mechanism.

Printing device 100 may further include endless belt regeneration unit 106.

Endless belt regeneration unit 106 cleans endless belt 201 automatically while transfer device 200 is incorporated in printing device 100. Endless belt regeneration unit 106 removes a residue of functional material 170 or the like and regenerates transfer performance of endless belt 201 by, for example, spraying vapor on endless belt 201.

Printing device 100 may further include a cutting unit (not illustrated) for cutting thin-film 120 or thin-film printed body 160 into a desired shape before transfer unit 105. The cutting unit can assist simpler makeup by, for example, processing thin-film printed body 160 for local makeup, such as rouge and eye shadow, into a shape convenient for transfer to a place for the local makeup.

With the foregoing configuration, when transfer device 200 affixes thin-film printed body 160 transferred from printing device 100 on the human body, functional material 170 that is printed based on makeup information is easily affixed on the skin to produce a visual effect as if makeup has been applied. This enables people who do not have sufficient knowledge or techniques about makeup and people who cannot take time for makeup to apply makeup easily, quickly, and safely.

Next, operations of transfer device 200 and printing device 100 according to the first exemplary embodiment of the present disclosure will be described with reference to FIG. 3, FIG. 4, and FIG. 5A to FIG. 5E. FIG. 5A to FIG. 5E are diagrams each illustrating the operations of printing device 100 and transfer device 200.

First, thin-film sheet feeder 101 supplies thin-film sheet 110 from outside of printing device 100 into inside of printing device 100.

Next, thin-film sheet 110 including thin-film 120 and first support 130 is sent to printing unit 104. Here, printing unit 104 prints functional material 170 corresponding to makeup information from outside on thin-film 120 in accordance with printing information generated by controller 103.

At this time, controller 103 communicates with, for example, makeup information terminal 140 that is outside of printing device 100 to obtain the makeup information. Controller 103 generates the printing information about what printing is to be made on thin-film 120 in order to apply the makeup, and transmits the printing information to printing unit 104 as a control signal.

Based on the control signal, printing unit 104 drives a head to print functional material 170 on thin-film 120.

As a result, thin-film printed body 160 is formed with functional material 170 laminated on thin-film 120.

As functional material 170, it is possible to select not only a cosmetic agent for female makeup but also every material that can perform functions required in medical or other fields.

In addition, preferably a thickness of thin-film 120 is between 10 nm and 10,000 nm inclusive (between 10 nm and 10 μm inclusive). Particularly, a thickness of between 10 nm and 500 nm inclusive is more preferable. This is because a test result shows that the adhesive property to skin is good when the thickness is 500 nm or less.

Furthermore, it is possible to use an arbitrary material as a material for biocompatible thin-film 120 with no particular limitation. Examples of the materials for the thin-film include polyesters represented by polyglycolic acid, polylactic acid, polycaprolactone, polyethylene succinate, and polyethylene terephthalate, or copolymers thereof; polyethers represented by polyethylene glycol and polypropylene glycol; polyamides represented by nylon, polyglutamic acid, and polyaspartic acid, or salts thereof; polysaccharides represented by pullulan, cellulose, starch, chitin, chitosan, alginic acid, hyaluronic acid, and cornstarch, or salts thereof; silicones represented by acrylic silicone and trimethylsiloxysilicate; acrylic acids represented by alkyl acrylate, silicone acrylate, and amide acrylate, or copolymers thereof; polyvinyl alcohol; polyurethane; polycarbonate; polyacid anhydride; polyethylene; and polypropylene.

Here, the makeup information means information for printing a material that supports some functional components such as components for wide variety of uses including cosmetic and medical uses on thin-film 120 to be affixed on skin. The present exemplary embodiment only discloses makeup as an example.

For example, when the cosmetic use is considered, the makeup information is information for makeup of part or all of a face, and means wide-ranging makeup from makeup for concealing part of spots to full makeup of the entire face. However, when uses in other fields, for example, a medical use and the like are considered, the makeup information may also be used for a region other than a face.

Furthermore, the makeup information may be provided by analyzing makeup optimized for an individual user, and may be provided as information for applying the latest makeup or makeup for a specific celebrity as an application installed in makeup information terminal 140 or as cloud service from a server via a network.

In addition, when the medical use is considered, a use for concealing a scar, such as a bruise or a burn, and a use for printing a medicinal ingredient to be used on an affected part like an adhesive plaster can be considered.

That is, use functions widely needed can be suitably added by causing a functional component needed for each use to be supported regardless of a use field.

Here, thin-film printed body 160 may be used so that a medical or cosmetic effect is obtained by causing a medical component or a cosmetic component to penetrate inside of the thin-film, whereas thin-film printed body 160 may be used so that a functional material, such as a cosmetic agent, does not penetrate inside of the thin-film. That is, it is possible to select among various implementations depending on the use of the supported (printed) functional component.

In addition, it is possible to freely design and print by oneself a seal for cheering sports, a seal to be affixed on a face in an amusement park, and the like.

Furthermore, with makeup information terminal 140, it is also possible to analyze a user's individual beauty information from image information obtained by photographing the user's face, and to customize printing of functional material 170. For example, it is also possible to have a skin-color correction function for matching a color with the user's skin color.

It is also possible to load individual face information to print an active ingredient (for example, a moisturizer, a sunscreen, a skin-whitening agent) only on a necessary place.

In addition, extraction of a characteristic point of the user's face makes it possible to print a positioning symbol, an arrow indicating a movement direction, and the like that assist the user in affixing the film simultaneously with functional material 170, thereby assisting simpler makeup.

In printing unit 104, thin-film sheet 110 on which functional material 170 is printed is humidified by humidifier 102 before being sent to transfer unit 105. Such humidification improves softness of thin-film 120, and lowers an adhesive force of an interface (C) between first support 130 and thin-film 120.

Humidifier 102 facilitates and ensures transferring of thin-film printed body 160 from first support 130 to endless belt 201 in subsequent transfer unit 105.

Then, humidified thin-film sheet 110 on which functional material 170 is printed is sent to transfer unit 105. Here, only thin-film printed body 160 is transferred on endless belt 201 of transfer device 200 installed in advance in printing device 100.

At this time, in transfer unit 105, endless belt 201 of transfer device 200 is brought into intimate contact with a functional material 170 side of thin-film printed body 160 on first support 130.

Here, an adhesive force at an interface (C) between first support 130 and thin-film 120, and an adhesive force at an interface (A) between a surface of thin-film 120 on which makeup information is printed and endless belt 201 are set in advance such that the former adhesive force is smaller than the latter adhesive force (C<A). Accordingly, thin-film printed body 160 separates from first support 130 on a thin-film 120 side, and comes into intimate contact with endless belt 201 of transfer device 200 on a functional material 170 side. As a result, thin-film printed body 160 is transferred well from first support 130 to endless belt 201.

The user waits for thin-film printed body 160 with functional material 170 or the like printed on thin-film 120 by printing device 100 to be transferred on endless belt 201 of transfer device 200. The user then detaches transfer device 200 from printing device 100.

The user then holds grip portion 203 of transfer device 200, presses transfer device 200 against a desired place on the human body, and slowly moves transfer device 200 in a right direction according to printing content.

Then, rotating rolls in transfer device 200 rotate, and a winding surface of endless belt 201 moves, thereby allowing transfer of thin-film printed body 160 on which makeup information is printed from endless belt 201 onto the human body.

At this time, a positioning mark, an arrow indicating a movement direction, and the like printed on thin-film printed body 160 allow the user to operate transfer device 200 based on the mark or the arrow, thereby assisting simpler makeup.

In addition, transfer device 200 may be configured to be an automatic transfer device by mounting a sensor for detecting a shape of the human body or the like such that the positioning mark is automatically positioned in a corresponding place on the human body. Moreover, transfer device 200 may be configured such that makeup information terminal 140 recognizes a position of transfer device 200 and navigates transfer device 200 to a transfer position on the skin, thereby achieving transfer to an appropriate position on the human body. Furthermore, transfer device 200 may include a transmitting unit for providing positional information to work with makeup information terminal 140 and to further navigate transfer device 200 to an appropriate position.

Since two rollers 202 apply moderate tension in moderate width, endless belt 201 can transfer thin-film printed body 160 well with an adhesive property even on an uneven surface on the human body.

A transferring operation in transfer device 200 will be described with reference to FIG. 4.

After being detached from printing device 100, transfer device 200 is pressed against a desired place of the human body by the user.

At this time, an adhesive force A and an adhesive force B are set to satisfy a relationship of A<B in advance, the adhesive force A being at an interface (A) between endless belt 201 and a surface of thin-film printed body 160 on which functional material 170 is printed, the adhesive force B being at an interface (B) between the human body (skin) and thin-film 120. Accordingly, thin-film printed body 160 separates from endless belt 201 of transfer device 200 on a functional material 170 side, and comes into intimate contact with the skin on a thin-film 120 side. As a result, thin-film printed body 160 is transferred well from endless belt 201 to the skin. A magnitude relationship of the adhesive forces can be evaluated by a quantitative evaluation using devices, such as a rheometer and a bondtester, and by visually determining a proportion of thin-film printed body 160 being transferred when thin-film printed body 160 is affixed on a base material or the skin.

In this way, thin-film printed body 160 that is thin-film 120 on which functional material 170 is printed is transferred to the skin by transfer device 200, and the makeup is completed.

With the foregoing configuration, when transfer device 200 is detached from printing device 100, pressed against a desired place on the human body, and moved, it is possible to easily transfer thin-film printed body 160 on which functional material 170 or the like is printed.

The present exemplary embodiment eliminates a concern about an influence of a printing agent on a living body because a printing surface of functional material 170 of thin-film printed body 160 is always on an opposite side of a surface on a side that is to be transferred to skin.

That is, since only a biocompatible thin-film side is transferred to the human body, a user having skin weak to, for example, a cosmetic agent, can also apply makeup easily and freely without limitation to a cosmetic agent or the like.

It is needless to say that the present disclosure is not limited to the aforementioned exemplary embodiment and that various modifications may be made appropriately within the intended scope of the present disclosure.

The configuration of the present disclosure enables an ultrathin thin-film to be simply transferred to an adherend such as a human body without damage to the thin-film itself, the thin-film having an adhered functional material such as a cosmetic agent used, for example, in cosmetic and medical fields, the thin-film requiring careful handling.

This enables people who do not have sufficient knowledge or techniques about makeup and people who cannot take time for makeup to apply beautiful, safe makeup easily and quickly without assistance.

The invention claimed is:

1. A transfer system comprising:

[a plurality of rollers configured to provide a rotating function;

an endless belt installed on the plurality of rollers;]

a thin-film having a first surface and a second surface opposite to the first surface; [and]

a functional material adhered on the first surface, the functional material including at least one *selected from the group consisting* of a cosmetic material and a medical material[, wherein]*;*

*a grip portion for a user to grip; and*

*a transfer apparatus having a third surface on which* the thin film and the functional material are retained [on the endless belt] so that the functional material is in contact with the [endless belt] *third surface*, *wherein:* the thin film and the functional material are transferred to an adherend so that the second surface is in contact with the adherend, and the thickness of the thin-film is between 10 nm and 500 nm inclusive.

2. The transfer system according to claim 1, wherein*:* the thin-film and the functional material constitute a thin-film printed body, and the thin-film printed body is formed by a printing device and transferred to the [endless belt] *third surface*.

[3. The transfer system according to claim 1 or 2, further comprising:

a grip portion for a user to grip.]

4. The transfer system according to claim [3] *1*, wherein*:*

*the transfer apparatus comprises a belt having the third surface, and* the transfer system transfers the thin-film printed body to the adherend by operation of the grip portion to move the [endless] belt with the [endless] belt being in contact with the adherend.

5. [The transfer system according to claim 1, wherein] *A transfer system comprising:*

*a thin-film having a first surface and a second surface opposite to the first surface;*

*a functional material adhered on the first surface, the functional material including at least one selected from the group consisting of a cosmetic material and a medical material; and*

*a transfer apparatus having a third surface on which the thin film and the functional material are retained so that the functional material is in contact with the third surface, wherein:*

*the thin film and the functional material are transferred to an adherend so that the second surface is in contact with the adherend,*

*the thickness of the thin-film is between 10 nm and 500 nm inclusive, and* an adhesive force A and an adhesive force B satisfy a relationship of A<B, the adhesive force A being at an interface between the [endless belt] *third surface* and the thin-film, the adhesive force B being at an interface between the thin-film and the adherend.

6. The transfer system according to claim 1, wherein the adherend is human skin.

7. A transfer system comprising:

[a plurality of rollers configured to provide a rotating function;

an endless belt installed on the plurality of rollers;]

a thin-film having a first surface and a second surface opposite to the first surface; [and]

a functional material adhered on the first surface*; and*

*a transfer apparatus having a third surface on which the thin film and the functional material are retained so that the functional material is in contact with the third surface*, wherein:

the functional material includes a cosmetic material, the cosmetic material includes at least one *selected from the group consisting* of a moisturizer, a sunscreen and a skin-whitening agent,

[the thin film and the functional material are retained on the endless belt so that the functional material is in contact with the endless belt, and]

the thin film and the functional material are transferred to [the] *a* living body so that the second surface is in contact with the living body,

*the thin-film and the functional material constitute a thin-film printed body, and*

*the thin-film printed body is formed by a printing device and transferred to the third surface.*

[8. The transfer system according to claim 7, wherein:

the thin-film and the functional material constitute a thin-film printed body, and the thin-film printed body is formed by a printing device and transferred to the endless belt.]

9. The transfer system according to claim 7, further comprising:

a grip portion for a user to grip.

10. The transfer system according to claim 7, wherein the [endless belt has at least one of] *third surface is* a surface having been treated to increase a hydrophilic property, a surface having an uneven pattern, [and] *or* a surface having a temperature-responsive polymer.

11. The transfer system according to claim 7, wherein an adhesive force A and an adhesive force B satisfy a relationship of A<B, the adhesive force A being at an interface between the [endless belt] *third surface* and the thin-film, the adhesive force B being at an interface between the thin-film and the living body.

12. A transfer system comprising:

[a plurality of rollers configured to provide a rotating function;

an endless belt installed on the plurality of rollers;]

a thin-film having a first surface and a second surface opposite to the first surface; [and]

a functional material adhered on the first surface*; and*

*a transfer apparatus having a third surface on which the thin film and the functional material are retained so that the functional material is in contact with the third surface*, wherein:

the functional material includes a medical material, the medical material includes a medicinal ingredient,

[the thin film and the functional material are retained on the endless belt so that the functional material is in contact with the endless belt, and]

the thin film and the functional material are transferred to an adherend so that the second surface is in contact with the adherend*, and*

*the thin-film and the functional material constitute a thin-film printed body, and*

*the thin-film printed body is formed by a printing device and transferred to the third surface.*

[13. The transfer system according to claim 12, wherein:

the thin-film and the functional material constitute a thin-film printed body, and the thin-film printed body is formed by a printing device and transferred to the endless belt.]

14. The transfer system according to claim 12, further comprising:

a grip portion for a user to grip.

15. The transfer system according to claim 12, wherein the [endless belt has at least one of] *third surface is* a surface having been treated to increase a hydrophilic property, a surface having an uneven pattern, [and] *or* a surface having a temperature-responsive polymer.

16. The transfer system according to claim 12, wherein an adhesive force A and an adhesive force B satisfy a relationship of A<B, the adhesive force A being at an interface between the [endless belt] *third surface* and the thin-film, the adhesive force B being at an interface between the thin-film and the adherend.

* * * * *